United States Patent [19]

Murry et al.

[11] Patent Number: 5,371,003
[45] Date of Patent: Dec. 6, 1994

[54] ELECTROTRANSFORMATION PROCESS

[75] Inventors: Lynn E. Murry, Portola Valley; Ralph M. Sinibaldi, Fremont; Paul S. Dietrich, Palo Alto; Sharon C. H. Alfinito, Fremont, all of Calif.

[73] Assignee: Sandoz Ltd., Basel, Switzerland

[21] Appl. No.: 126,138

[22] Filed: Sep. 23, 1993

Related U.S. Application Data

[63] Continuation of Ser. No. 47,175, Apr. 14, 1993, abandoned, which is a continuation of Ser. No. 817,703, Jan. 7, 1992, abandoned, which is a continuation-in-part of Ser. No. 674,415, Mar. 22, 1991, abandoned, which is a continuation of Ser. No. 582,824, Sep. 14, 1990, abandoned, which is a continuation of Ser. No. 389,079, Aug. 3, 1989, abandoned, which is a continuation-in-part of Ser. No. 209,401, Aug. 2, 1988, abandoned, which is a continuation-in-part of Ser. No. 190,286, May 4, 1988, abandoned, which is a continuation-in-part of Ser. No. 27,712, May 5, 1987, abandoned.

[51] Int. Cl.$^5$ .............................................. C12N 15/87
[52] U.S. Cl. .............................. 435/172.3; 435/173.6; 435/173.5; 435/6; 935/19; 935/52
[58] Field of Search ............... 435/172.3, 173.6, 173.5, 435/6; 935/19, 52

[56] References Cited

FOREIGN PATENT DOCUMENTS

| | | |
|---|---|---|
| 1208146 | 7/1986 | Canada . |
| 142924 | 5/1985 | European Pat. Off. . |
| 257472 | 8/1987 | European Pat. Off. ..... C12N 15/00 |
| 289479 | 4/1988 | European Pat. Off. ..... C12N 15/00 |
| 270356 | 6/1988 | European Pat. Off. . |
| 8301176 | 4/1983 | WIPO . |
| 8501856 | 5/1985 | WIPO . |

OTHER PUBLICATIONS

Wong et al. 1982 Biochem Biophys Res. Comm. 107 (2): 584–587.
Teissie et al. 1981 Journal Physiol (Paris) 77:1043–1053.
Xie et al. 1990 Biological Abstracts #136400.
Xie et al. 1990 Biophysical Journal 58 (4):897–904.
Fromm et al. 1985 Proc. Natl Acad Sci USA 82:5824–5828.
Fromm et al. 1986 (Feb.) Nature 319:791–793.
Niesel et al. 1983 Focus 5 (4):6–7.
Kenis et al. 1986 Physiol Pl 68(3):387–390.
Mukerji et al. 1975 Indian J of Exp. Biol. 13(6):575–577.
Brodelius 1986 In Handbook of Pl. Cell Culture; Evans (ed.); MacMillan Publisher; NY pp. 304–306.
de la Pena 1987 "Transgenic Rye Plants Obtained by Injecting DNA into Young Floral Tillers" Nature 325(6101):274–276.
Paszkowski, J. et al. 1984, "Direct Gene Transfer to Plants" EMBO J. 3(12):2717–2722.
Goldman et al. 1987, "Transformation of Zea Mays by Agrobacterium Tumefaciens: Evidence for Stable Genetic Alterations" J. Cell Biochem. Suppl. 0 (11 part B).
Morikawa, J. et al. "Gene Transfer Into Intact Plant Cells by Electroinjection Through Cell Walls and Membranes" Gene 41(1):121–124.
Spandidos, D. 1985, "Transformation of Mammalian Cell by Iontophoretic Pricking of Iontophoretic Microinjection" Eur. J. Cell Bio. 37:234–239.
Ocho, M. et al. 1981, "Microinjection of Nucleic Acid Into Cultured Mammalian Cells by Electrophoresis" Acta Med Okavama 35(5):381–384.

Primary Examiner—Patricia R. Moody
Attorney, Agent, or Firm—Lynn Marcus-Wyner; Allen E. Norris

[57] ABSTRACT

Novel processes for introducing DNA into plant material utilizing non-pulsed electric current, and plant cell lines, differentiated plant tissues and plants produced by said processes.

18 Claims, 2 Drawing Sheets

ELECTROTRANSFORMATION PROCESS

This is a continuation of application Ser. No. 08/047,175, filed Apr. 14, 1993, now abandoned; which is a continuation of application Ser. No. 07/817,703, filed Jan. 7, 1992, now abandoned; which is a continuation-in-part of application Ser. No. 07/674,415, filed Mar. 22, 1991, now abandoned; which is a continuation of application Ser. No. 07/582,824, filed Sep. 14, 1990, now abandoned; which is a continuation of application Ser. No. 07/389,079, filed Aug. 3, 1989, now abandoned; which is a continuation-in-part of application Ser. No. 07/209,401, filed on Aug. 2, 1988, now abandoned; which is a continuation-in-part of application Ser. No. 07/190,286, filed on May 4, 1988, now abandoned; which is a continuation-in-part of application Ser. No. 07/027,712, filed on May 5, 1987, now abandoned.

The present invention relates to processes for introducing DNA into monocotyledonous and dicotyledonous plant material by utilization of non-pulsed electric current for a sufficient time to effect transformation. The process provides for the direct transfer of DNA into intact monocotyledonous and dicotyledonous plant material.

BACKGROUND

There are basically two approaches which have successfully been used to transform plants genetically, but each method has limitations when applied in particular to monocotyledonous plants (monocots) and particularly to the commercially important crops, the cereals.

The first method utilizes *Agrobacterium tumefaciens*, which is a soil microbe containing a Ti plasmid that transfers DNA from the plasmid to the genome of the infected plant. The method is basically restricted to dicotyledonous plants since monocots are usually not susceptible to Agrobacterium. Although the genetic transformation of Asparagus using this method has been disclosed [WO 86/03776] and Grimsley et al., *Nature* 325:177-179 (1987), have reported the transfer of DNA into cereals via Agrobacterium, it had at the time of this invention not yet been demonstrated that actual transformation i.e., uptake and integration of the exogenous DNA with the host cell genome or expression of the desired new traits, may occur.

The second transformation method involves direct transfer of DNA into plant protoplasts. Such direct transfer can be obtained, for example, by chemically stimulated uptake using polyethylene glycol [Paszkowski et al., *Meth. Enzym.* 118:668-684 (1986)] by a high-voltage pulse (electroporation) which punches transient holes in the protoplast membrane. (See, e.g., Fromm et al., *Nature* 319:791-793 (1986)) or by particle bombardment (Sanford et al. *Part. Sci. Technol* 5(1) 27-37 (1987). The direct transfer method depends on a tissue culture system that allows regeneration of mature, fertile plants from protoplasts. However, in the cereals, it had at the time of this invention been possible to regenerate only rice from protoplasts. Attempts to regenerate maize protoplasts into fertile plants had been unsuccessful. See, e.g., Graves et al., *Theor. Appl. Genet.* 54:209-214 (1979).

It has recently been demonstrated that naked RNA can be introduced and expressed in whole cells of dicotyledonous plants (dicots) by means of electroporation. Morikawa et al., *Gene* 41:121-124 (1986), have shown that tobacco mosaic virus (TMV) RNA may be introduced into mesophyll cells of Nicottana, through intact cell walls. This is the first and only presently known example of introduction of naked genetic material into intact cells and is stated to have produced cells with a low survival rate. It was not clearly demonstrated that the cells were actually transformed rather than infected. Additionally, the procedure has been shown to work only on individual cells of dicotyledonous plants. Even if electroporation of individual monocot cells was to be successful in the future, there is still the unsolved problem of regenerating monocot, and in particular maize cells into whole fertile plants.

DISCLOSURE OF THE INVENTION

Figure 1:
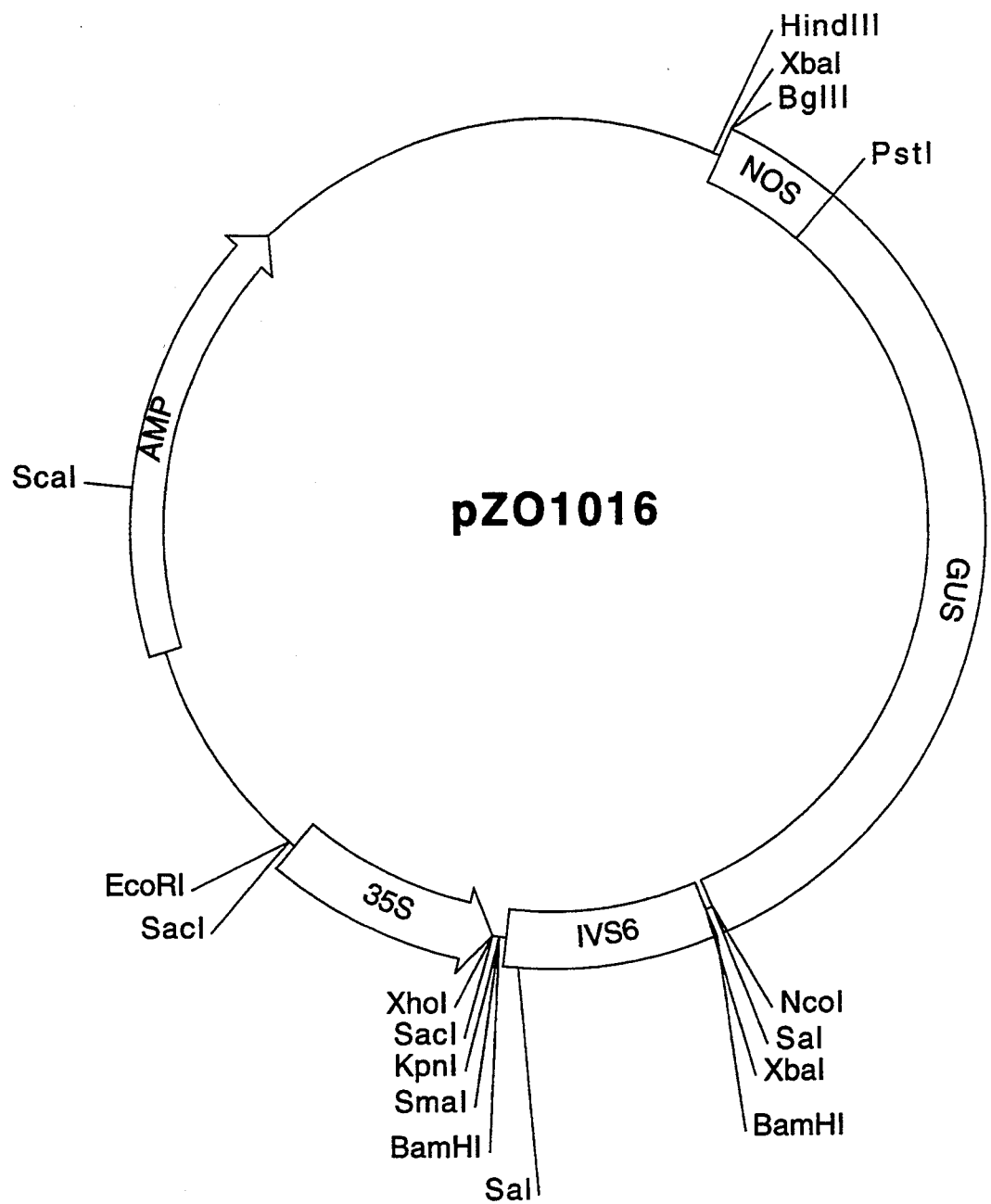
FIG. 1 shows a plasmid map for plant transformation vector p ZO 1016.

The present invention relates to a novel process for preparing transformed plant cell material which is genetically stable, which process comprises the transformation of plant cell material using long-term non-pulsed electric current (electrotransformation).

More particularly, the process of the present invention comprises placing the plant material and a transformation solution comprising DNA in close proximity to each other within a field which is subject to the passage of an electrical current in a direction to transport the DNA by the current toward and into the plant material, and passing an electric current through said field for a time sufficient to effect such transformation. In a preferred embodiment, the transformation solution further comprises a membrane-permeating agent, which is also transported by the electric current.

The present invention utilizes a more constantly, longer applied (non-pulsed) electric force which transports the DNA to and through the cell wall and membrane, in contrast to electroporation or electroinjection techniques in which short pulses of electric current are used to punch transient holes in the cell membrane to allow entrance of DNA.

The method of this invention has several advantages. It allows the penetration of numerous layers of cells such that whole tissues rather than single cells may be used. The cells are not injured; they maintain their viability and can be used for the production of mature, fertile plants. The method also allows for the transformation of plants which had previously not been successfully transformed.

The invention also relates to a method for producing a transformed fertile plant comprising contacting plant material with a transformation solution comprising DNA in the presence of an electric current for a time sufficient to effect transformation and culturing the thus transformed plant material under culture conditions.

Therefore, in one embodiment, the present invention is directed to a plant cell line, cultivar or variety produced by the above method enriched in cells having in their genome DNA originating from a source other than the host or recipient cell and capable of regenerating into fertile plants.

In yet another embodiment, the present invention is directed to differentiated plant material comprising cells that are transformed by DNA such as plants, plant organs, seeds, pollen and the like.

These and other embodiments of the present invention will be readily apparent to those of ordinary skill in the art from the following description.

DETAILED DESCRIPTION

In describing the present invention, the terminology used herein is intended to be used in accordance with its current accepted meaning in the art. To the extent that accepted meanings do not exist or are ambiguous, the following definitions are controlling:

"Electrotransformation" (ET) is the process whereby genetic material is taken up into a host cell and subsequently becomes part of the host cell genome by utilization of long-term, non-pulsed electric current for a sufficient time to effect transformation.

Plant "tissue" is a population of cells.

"Embryo" is the stage in development in which specific organs or organ systems are not visibly differentiated, but cell compartments which will give rise to organs are present.

"Callus" is the cluster of plant cells that results from tissue-culturing a single plant cell or tissue, "CM(30)" media is artificial corn medium, the composition of which is described in Table A.

"MTM" media is artificial liquid medium useful for culturing maize tassels, the composition of which is described by Pareddy, Greyson and Walden, *Planta* 170:141 (1987).

"BSS" media is artificial medium for Brassica stem strips, the composition of which is described in Table B.

"TMM" media is artificial medium for culturing tomato embryos, the composition of which is illustrated in Table C.

A plant "protoplast" is a plant cell which has had the cell wall removed, usually by enzyme digestion, but which is bounded by a cell membrane.

"Meristem" or "meristematic tissue" are cells that are fully capable of further division, giving rise, in turn, to embryonic, primary or secondary tissue.

A cell "tranformed" by DNA is a cell that contains said nucleic acid, or a descendant thereof through mitosis or meiosis which still retains the said DNA sequence in its genome.

"TAE" = tris-acetate EDTA.

"BMS" = Black Mexican Sweet.

"BSA" = Bovine Serum Albumin.

The present invention envisages the transformation of plant cell material with DNA. The ability to transform, for example, crops such as maize with DNA or other nucleic acid and to regenerate plants therefrom is of obvious importance to the agricultural industry.

The DNA employed in the process of the invention would be conveniently in vector form, preferably in plasmid form, which plasmid is genetically manipulated using standard recombinant DNA techniques well known to those skilled in the art, so as to contain DNA with which it is desired to transform the plant material.

Plant material transformed with DNA, or cells descended therefrom via mitosls or meiosis, will be identifiable structurally since the portion of the genome incorporating said DNA sequence will be substantially non-homologous to the same genomic region in a cell from the pre-transformation source of the tissues, i.e. the wild-type variety or strain.

DNA suitable for use in this invention would include any DNA originating from a source other than the host or recipient cell. Examples of such valuable DNA which may be used in the electrotransformation process of this invention could thus include DNA encoding zein, the storage protein of corn, or tissue-specific promoters such as those from maize genes that can be used in chimeric constructions (e.g., the alcohol dehydrogenase (ADH) promoter which is inducible in roots).

A preferred class of DNA suitable for use in this invention can be classified as foreign DNA. Foreign DNA may be defined as any DNA originating from a source other than the host or recipient plant. Foreign DNA includes, for example, non-host plant DNA, synthetic DNA sequences, sequences produced by recombinant DNA techniques, bacterial, fungal, viral or animal DNA sequences and so on.

Suitable foreign DNA can include non-host plant promoters such as T-DNA promoters from Ti and Ri plasmids, plant virus promoters (e.g., CaMV, TMV, BMV, etc.) and the like. Suitable foreign DNA can also include foreign structural sequences from the genes for chloramphenicol acetyl transferase (CAT), neomycin phosphotransferase II (npt-II), nopaline synthase (NOS), β-galactosidase (β-Gal), β-glucuronidase (GUS), the glyphosate resistance gene (EPSP, which is the enzyme conferring resistance to glyphosate-5-enolpyruvylshikimate-3-phosphate synthase) and the *Bacillus thuringienesis* (B.t.) genes for a crystal protein insect toxin. See, e.g., Adang et al (1985) *Gene* 36:289–300; Wong et al., *Proc. 9th Int. Spore Cong.*, pp. 104–109 (Hoch & Setlow eds. 1985). Examples of Bacillus thuringiensis type genes include the B.t. var kurstaki (B.t.k.) gene coding for a protein toxin toxic to lepidopterous larvae, particularly Noctuidea, more particularly *Heliothis zea* and *Heliothis virescens* and Spodoptera species such as *Spodoptera exigua* and *Spodoptera frugiperda;* and the B.t. var tenebrionis (B.t.t.) gene coding for a protein toxin toxic to Coleoptera pests, particularly Chrysomelidae, more particularly Diabrotica species such as *D.longicornis, D.undecimpunctata* and *D. virgifera* and Leptinotarsa species such as *L.decemlineata*. The aforementioned Heliothis, Spodoptera, and Diabrotica species are pests infecting crops such as corn. Foreign DNA can also include synthetic genes, such as synthetic DNA sequences based upon native host plant genes (e.g., an altered or mutated zein gene which changes the amino acid composition of the maize storage protein). The foreign DNA of the present invention can involve chimeric constructions such as promoter/structural sequence combinations heterologous to each other. Examples of such heterologous constructions include a B.t. toxin gene under the control of the ADH promoter, and selectable markers, such as the CAT or npt-II structural sequence under the control of a T-DNA promoter or a CaMV promoter.

DNA sequences for transformation may be constructed according to standard recombinant methods. See, e.g., DNA CLONING, Vol. I & II (D. Glover, ed. 1985); Maniatis et al., MOLECULAR CLONING: A LABORATORY MANUAL (1982), both of which are incorporated herein by reference.

Other DNA sequences or combinations of such which may be used in the present invention will be readily apparent to one of ordinary skill in the art.

For the electrotransformation process of the present invention, any non-protoplastic plant material may be utilized. Thus, for example, plant tissues, embryos, meristematic tissue such as tassel or ear meristem, axillary buds, stem strips, callus or cell suspensions may be transformed. Embryos are particularly preferred. The plant material is conveniently in excised form.

In some cases it may be advantageous to subject the plant material to enzymatic digestion prior to electrotransformation.

Suitable digestion media contain protoplasting enzymes such as cellulase, hemicellulase, pectinase, etc. A typical such medium is shown in Table D hereinafter. The period of digestion will depend on the plant-material and enzymes employed but will usually be for a period of from 20 to 90 especially from 40 to 60 minutes.

Orientation of the plant material with respect to the directional movement of DNA can also affect the frequency of ET-events. Thus in the case of corn embryos the highest frequency was found in the coleoptyle/shoot tissues followed by scutellum. Orientation of the embryonic axis and the front side of the scutellum towards DNA flow optimizes ET-frequency.

Obviously for the regeneration of fertile plants, maximization of the ET events in the shoot/reproductive cells would be desirable and this can be optimized e.g. by partial or complete removal of other receptive tissues such as coleoptyle and scutellum prior to digestion and orientation of the cut surface toward the advancing DNA-solution.

Although transformation can be effected in the absence of a membrane-permeating agent, it is generally preferred that the transformation solution includes a membrane-permeating agent, a chemical which assists or otherwise allows the uptake of molecules which normally cannot enter cells. Preferred polar membrane-permeating agents are those which are carried, in association with the DNA, to and through the cell membrane when tension resulting from the electrical current is applied. Suitable examples of polar membrane-permeating agents include dimethyl sulfoxide (DMSO), lysolecithin and detergents such as sodium dodecyl sulphate and Triton-X, preferably DMSO. The concentrations of such membrane-permeating agent used should be sufficient to render the cell membrane temporarily permeable but without destroying the integrity of the intracellular organelle membranes. Such concentrations may vary within wide ranges and will, e.g. depend on the plant material or species involved. More resistant species may stand, for example, a concentration of 10% DMSO. In general, good results will be obtained with a concentration of polar membrane-permeating agent of from about 1% to about 4%, preferably about 2%, by weight of the transformation solution.

The transformation solution may optionally include a tracking dye which is useful to indicate the direction and progress of the DNA molecules in the electrophoresis system. Such dyes may be chosen from bromocresol green, bromophenol blue and xylene cyanol, for example. Use of such dyes is well known in the art.

In a preferred process of the present invention, the plant material is excised and is placed in wells in an agarose gel in a horizontal gel electrophoresis system. A transforming solution comprising plasmid DNA and DMSO is placed in wells in close proximity to those containing the plant material. A tracking dye may optionally be included in the solution to follow the advance of the DNA molecules. Low voltage non-pulsed electric current is applied, running in the direction from the DNA-containing transformation solution toward and past the plant material. Thereafter, the material may be washed with sterile liquid and placed on solid medium for a period of recovery, depending on the age and size of the material treated. (Younger and/or smaller tissues often require a longer recovery period prior to the selection process in order to recover from trauma associated with electrotransformation.) The tissues are normally kept on the medium for 2–3 days, after which the successfully transformed tissues are selected, by, for example, exposure to a selective antibiotic or herbicide. Those tissues which germinate (develop roots and shoots in the case of embryos) or grow and develop chlorophyll on the selection medium have acquired resistance by incorporation of the transforming DNA.

Particularly useful for subsequent regeneration are transformed cells from the scutellum of the embryo.

The voltage of the continuous electric current adequate to carry out the present invention should be sufficient to transport the DNA in the transformation solution toward and into the plant material to be transformed in order to effect transformation but should not exceed that which would substantially damage the plant cells. The voltage to be employed may vary and will depend on various factors such as the type and form of the plant material employed and the time during which the voltage is applied. Thus for example 50% of corn embryos will survive when exposed to a current of 200 V for 5 minutes in a gel electrophoresis system. Voltages up to 110 V may be used without seriously damaging the corn embryo, although germination may be delayed. Voltages above 200 V should in general be avoided. On the other hand, transformation may still be obtained with a voltage as low as 8 V. In general, satisfactory results will be obtained when applying an electric current of from about 30 V to about 140 V, preferably from about 50 V to 110 V and most preferably from 52 V to 80 V. In the gel electrophoreis system employed in the examples, the electrodes are 15 to 24 e.g. 18 cm apart. Thus, for example, the application of voltage of 50 V in such a system will result in an electric field strength of 50 V/18 cm or 2.78 V/cm. This gives an idea of the order of magnitude of electric field strength applied. The electric current strength produced in such systems will depend on, for example, the transformation solution and the gel employed and the voltages applied. In general, voltages of from 2 to 6 v/cm especially 4 or 5 v/cm produce satisfactory results.

The period of time of exposure to the electric current is dependent on the distance between the wells containing the plant material and the wells containing the transformation solution, on the concentration of the support gel and also on the size of the plant sample. Thus, the minimum period of time is that time necessary for the DNA in the transforming solution to flow into the plant material samples. For example, if the distance between the two sets of wells in 0.6–0.7% agarose is 1 mm at initiation of the current, at a voltage of 52 V it will take about 13 to 15 minutes for the transforming solution to move past the position of a corn embryo and it will take about 20 minutes for the solution to move past a larger tissue such as a tassel initial. In general, transformation may be obtained after exposure to the electric current for about 5 to about 25 minutes, preferably for about 10 to about 20 minutes. In the case of corn embryos for example a voltage of 4 v/cm for 20 minutes produced satisfactory results.

The distance between the sets of wells, i.e. those containing the plant material sample and those containing the transforming solution, is dependent on the strength of the transforming solution and the concentration of the support gel, such that the distance is preferably greater when the gel is more dilute. Furthermore, time is preferably greater when the gel is more concentrated.

In a preferred embodiment, the plant material is transformed by a selectable marker gene so that transformed material can be isolated. Examples of such marker genes are, for example, antibiotic resistance genes which encode for resistance to such antibiotics as kanamycin, hygromycin, neomycin and chloramphenicol; genes encoding for herbicide resistance, such as resistance to glyphosate; and color marker genes, such as the blue GUS or red gene for corn and luminescence genes such as the luciferase gene. The presence of these genes allows transformed plants or their cells to be identified, such as, e.g. by survival and growth in medium containing a selective antibiotic or following the application of a selective herbicide.

In another preferred embodiment, the plant material is transformed by genes coding for traits which have high commercial or agricultural value, such as resistance to insects, resistance to herbicides, resistance to viruses, resistance to fungi, or for enzymes which will interfere in particular biochemical pathways, such as those leading to the synthesis of essential amino acids.

In a particularly preferred embodiment, the plant material is transformed by plasmid DNA which contains an identifiable or a selectable marker gene and a DNA sequence or sequences encoding for other desired traits. This allows selection for the transformed tissue which can then be screened for expression of co-transferred but unselected gene(s).

Plant material transformed according to the process of the present invention may be grown and regenerated into fertile plants.

Genetically transformed healthy fertile monocotyledonous plants are novel. The invention accordingly provides monocotyledonous plant material comprising in its genome DNA originating from a source other than the host or recipient cell and capable of regenerating into healthy, fertile plants.

The term "healthy" as used herein is intended to distinguish the plants of the invention from plants which are naturally infected by viruses and the like.

The invention further provides healthy, fertile monocotyledonous plants comprising in their genome DNA originating from a source other than the host or recipient cell and parts thereof, in particular seeds of such plants.

Preferred monocotyledonous plant material or plants according to the invention are crops of the Gramineae family, particularly cereals including rice, wheat, the millets, barley, sorghum, rye, oats, triticale and corn; more particularly cereals selected from wheat, the millets, barley, sorghum, rye, oats, triticale and corn; and most particularly corn.

It should be appreciated that the method of the invention is also a convenient alternative method for transformation of dicotyledonous plants including Brassica species, tomatoes, sunflower, carrots, cucurbits, potatoes, soybean, cotton, tobacco and the like.

The following examples illustrate the invention but are not intended to limit its scope in any way.

Temperatures are given in degrees centigrade ('C.) and percentages (%) are by weight.

TABLE A

| CM(30) Medium (Liquid or Solid) | |
|---|---|
| MS major salts | |
| $NH_4NO_3$ | 1.65 g/l |
| $KNO_3$ | 1.90 g/l |
| $CaCl_2.2H_2O$ | 0.44 g/l |
| $MgSO_4.7H_2O$ | 0.37 g/l |
| $KH_2PO_4$ | 0.17 g/l |
| MS minor salts | |
| $H_3BO_3$ | 6.20 mg/l |
| $MnSO_4.H_2O$ | 16.80 mg/l |
| $ZnSO_4.7H_2O$ | 10.60 mg/l |
| KI | 0.83 mg/l |
| $Na_2MoO_4.2H_2O$ | 0.25 mg/l |
| $CuSO_4.5H_2O$ | 0.025 mg/l |
| $CoCl_2.6H_2O$ | 0.025 mg/l |
| Vitamins | |
| Thiamine HCl | 0.25 mg/l |
| L-asparagine | 13.2 mg/l |
| Glycine | 7.7 mg/l |
| Carbon Source | |
| Sucrose | 20 g/l |
| Agar (for solid) | 8 g/l |
| Distilled water to | 1 liter |

TABLE B

| BSS Medium | |
|---|---|
| 4X Difco salts mixture[1] | 500 ml/l |
| nicotinic acid | 0.5 mg/l |
| pyridoxine HCl | 0.5 mg/l |
| thiamine HCl | 1.0 mg/i |
| inositol | 100.0 mg/i |
| naphthalene acetic acid | 0.2 mg/l |
| benzyl adenine phosphate | 1.0 mg/l |
| sucrose | 30.0 g/l |
| agar (for solid) | 16.0 g/l |
| distilled water to | 1 liter |
| pH adjusted to | 5.8 |

[1]Difco salts mixture is a commercially available mixture of the Murashige & Skoogs ("MS") major and minor salts. 4X is the strength of the stock solution of the mixture.

TABLE C

| TMK Medium | |
|---|---|
| 4X Difco salts mixture | 250 ml/l |
| nicotinic acid | 0.5 mg/l |
| pyridoxine HCl | 0.5 mg/l |
| thiamins HCl | 1.0 mg/l |
| inositol | 100.0 mg/l |
| sucrose | 20.0 g/l |
| agar (for solid) | 8.0 g/l |
| distilled water to | 1 liter |
| ph adjusted to | 6.0 |

TABLE D

| BMS Protoplasting medium (PE) | |
|---|---|
| 1.0% | cellulase (Calbiochem) |
| 0.5% | hemicellulase (Rhozyme) |
| 0.02% | pectinase (Pectolyase Y23) |
| 0.5% | BSA |
| 0.05 ml | β-mercaptoethanol in 100 ml distilled water |
| $CaCl_2 2H_2O$ | 7.35 g/L |
| $NaC_2H_3O_2 3H_2O$ | 1.66 g/L |
| mannitol | 45.00 g/L |
| pH to 5.8 with KOH, filter sterilize and store at 4° C. | |

EXAMPLE 1

Into each of eight wells in a 0.7% agarose gel is placed one Stage 3 excised corn embryo (Pioneer 3780) (refrigerator—synchronized for 2–7 days). Into each of eight additional wells, running parallel to and 1 mm from the first eight wells, is placed transformation solution comprising 15 ul (10 ug) of plasmid DNA (H83E or H83R), 2 ul of bromophenol blue dye and 2% DMSO. The embryo is positioned in its well such that the side of the embryo containing the meristematic tissue is facing the wells containing the transformation solution.

Stage 3 corn embryos are described in Abbe & Stein, *Am. J. Botany* 41:285 (1984).

The plasmids H83E and H83R each comprise the pUC 8 plasmid with a cauliflower mosaic virus (CaMV) 35S promoter [nucleotides 7013 to 7436; see, Hohn, et ala., *Curr. Top. Microbiol. Immunol.* 96:193–236 (1982)], a hygromycin phosphotransferase (HPT) coding sequence [the Bam HI fragment from pLG83; see, Gritz and Davies, *Gene* 25:179–188 (1983)], and a nopaline synthetase (nos) terminator [nucleotides 682 to 437; see Bevan et al., *Nucleic Acids Research* 11:369–385 (1983)]. The HPT sequence is in the sense orientation relative to the promoter and terminator sequences in plasmid H83E and in the antisense orientation in plasmid H83R, relative to the rest of the plasmid. Thus if the vector portion of pH83R can be considered to be In a "clockwise" orientation, the promoter-HPT-terminator cassette of pH83R is in a "counter-lockwise" orientation. In plasmid pH83E, both the plasmid and the promoter-HPT-terminator cassette are "clockwise".

Each gel is placed in a horizontal gel electrophoresis system (BRL H6) with 450 ml of sterile tris-acetate-EDTA running buffer. Gels are exposed to an electric current of 52 V, running in the direction from the DNA to the embryos, for a period of either 10, 12.5 or 15 minutes. After exposure, the embryos are rinsed with sterile liquid CM(30) medium and placed on solid CM(30) medium for 3 days. The embryos are then transferred to CM(30) medium containing 100 ug/ml of hygromycin. The embryos are scored at 11 and 14 days after electrotransformation treatment, with the following results:

At 11 days all embryos from all treatments had germinated (had developed roots and shoots). At 11 and 14 days the seedlings recorded under Table E (out of a total of eight in each treatment) were green, indicating acquired resistance to hygromycin by incorporation of the pLG83 gene. Nontransformed, hygromycin-selected controls turned chalk white and ceased to grow.

TABLE E

| Day | Control* 0 min. | Number of Green Seedlings | | | | | |
|---|---|---|---|---|---|---|---|
| | | H83E | | | H83R | | |
| | | 10 | 12.5 | 15 min. | 10 | 12.5 | 15 min. |
| 11 | 8 | 4 | 4 | 4 | 6 | 3 | 3 |
| 14 | 8 | 4 | 4 | 2 | 6 | 3 | 3 |

*The positive control embryos were transformed as for the test but with a plasmid not containing the HPT gene sequence, after which they were placed on non-hygromycin containing medium thus demonstrating that the transformation does not affect the ability of the embryos to form seedlings.

EXAMPLE 2

At 14 days after treatment with the H83E or H83R plasmid DNA, the green seedlings from each test group in Example 1 are collected and ground up, and the nucleic acid is extracted following the cetyltrimethylammonium bromide (CTAB) procedures described by Rogers et al., *Plant Mol. Biol.* 5:69 (1985).

The harvested seedling tissue for each group is ground to a fine powder in liquid $N_2$ or dry ice and placed in a test tube. The mixture is warmed slowly to 65 and a solution of CTAB [2% CTAB (w/v), 100 mM Tris (pH 8.0), 20 mM EDTA (pH 80), 1.4M NaCl and 1% PVP (polyvinylpyrrolidone)] at 1 ul/mg is added, followed by heating at 65 for 3 min. An equal volume of phenol and sevag ($CHCl_3$:isoamyl alcohol at 24:1) is added and mixed. The mixture is centrifuged at 11 kx for 30 sec., after which the top phase is transferred to a new tube, and CTAB (10% weight/volume) and 0.7M NaCl are added. Centrifugation is repeated, and the top phase is again separated and diluted with CTAB and NaCl. One volume of CTAB precipitation buffer [1% CTAB, 50 mM Tris (pH 8.0) and 10 mM EDTA (pH 8.0)] is added with gentle mixing, and the mixture is centrifuged for 1 min. The supernatant is discarded; the pellet is dissolved in high salt Tris-EDTA [10 mM Tris (pH 8.0), 1 mM EDTA (pH 8.0) and 1M NaCl] and is heated to 65 for 10 min. After complete rehydration, the nucleic acids are reprecipitated with 2 volumes of ethanol and then pelleted by centrifugation for 13–15 min. in a cold room. Minigels were run on all samples and showed the presence of DNA.

For dot blot analysis, the extracted DNA is heated to 100°, 20×SSPE is added and the solution is cooled and transferred to a nitrocellulose membrane. It is hybridized with nick-translated DNA (BRL Kit lot #5210, and H83E). See, Rigby et al., *J. Mol. Biol.* 113:237 (1977). The nitrocellulose is rinsed in 2×SSPE and 0.1% SDS and then heated at 50° for 1 hr., followed by agitation in 1×SSPE and 0.1% SDS at room temperature for 1 hr. and then exposure to x-ray film. See, Maniatis et al. (1983) *Molecular Cloning: A Laboratory Manual* (Cold Spring Harbor Laboratory). The results of the dot blot analysis indicate strong hybridization-transformation occurred in 10% of treated samples.

SSPE in a 20× stock solution is made from 3.6M NaCl, 200 mM $NaH_2PO_4$ (pH 7.4) and 20 mM EDTA (pH 7.4).

EXAMPLE 3

Tassel initials (1.0–1.5 cm long) of maize (cvx. Oh 43 and Se60) are dissected aseptically, as described by Pareddy and Greyson, *Plant Cell Tissue Organ Cult.* 5:119–128 (1985), and kept on MTM media until electro-transformation treatment. Following the procedure of Example 1, the tassels and transforming solution comprising either a) 8 ul (10 ug) of H83E plasmid, 2% of DMSO and 29 ul of distilled water, or b) 15 ul (10 ug) of H83R plasmid, 2% of DMSO and 22 ul of distilled water are placed in a 0.7% agarose gel in an electrophorests system apparatus and exposed to an electric current of 52 V for 13 min. Following exposure, the tassels are removed to sterile CM(30) media with 50 ug/ml of gentamicin added (for antibacterial purposes) and are rinsed gently for a short period. They are then placed in sterile flasks containing 50 ml of MTM media and the flasks are placed on a window sill. Two days after treatment, 5 ug/ml of hygromycln is added to each flask.

Six days after addition of the hygromycin, 1 out of 3 H83R-treated tassels had died (had stopped growing and bleached white). Ten days after the addition, 2 out of 15 H83E-treated tassels had died. Thirteen days post-addition, 2 more H83E-treated tassels had died. The remaining tassels continued to grow and stay green through 25 days after addition of the hygromycin. One of the tassels treated with H83E produced pollen, as well.

EXAMPLE 4

Following the procedures of Example 1, stem strips (approx. 1×3×4 mm) taken from the upper two nodes of the shoot in the bud of broccoli, *Brassica oleracea* cv. italica CrGC-9 (Crucifer Genetics Cooperative-9) are placed in a 0.7% agarose gel in an electrophoresis system apparatus along with transformation solution comprising 15 ul (10 ug) of pZ025 plasmid DNA, 2 ul of bromophenol blue dye and 0.3 ul (2%) of DMSO, and exposed to an electric current of 52 V for about 15 min.

Plasmid pZ025 is the same as H83E (from Example 1) except that the HPT coding sequence consists of the nucleotides 197 to 1251, modified by replacement of a guanine at position 206 by an adenine.

Following exposure, the stem strips are removed to sterile BSS medium for a short time, then to selection medium containing 20 ug/ml of hygromycin for 1 week and finally to medium containing 5 ug/ml of hygromycin for 1 week. Twenty-four stem strips produced callus when removed to BSS media without hygromycin. After 2 months they generated shoots, and were transferred to soil in a mist chamber to generate roots.

Leaves from two hygromycin-selected Brassica were cut into pieces and subjected to secondary selection on BSS media containing 25 ug/ml hygromycin. These pieces remained green and formed shoots. When they were removed to BSS with ½ strength salts and no hygromycin, they also rooted.

Leaves of these same two primary transformants were also analyzed for the presence of the hygromycin gene. Each leaf (approx. 0.2 g) was frozen in liquid nitrogen and ground to a powder in a mortar. 1.5 ml ice cold sucrose buffer (containing 15% sucrose, 50 mM TRIS pH 8.0, and 50 mM EDTA) and 0.25M NaCl were added to the tissue in the mortar and grinding was continued. The slurry was poured into a 5 ml Wheaton ground glass homogenizer and ground by hand for 5–10 passes. The slurry was then transferred to a 1.6 ml eppendorf tube and centrifuged for 3 min at 6500 rpm. The crude nuclear pellet was then resuspended in 0.5 ml of ice cold sucrose buffer (as above, but without NaCl). 1 $\mu$l diethylpyrocarbonate was added and the suspension was vortexed at room temperature. Next, 5 $\mu$l of 20% SDS was added and vortexed, then heated at 70° C. for 10 minutes. 50 $\mu$l of 5M potassium acetate was added and the solution was vortexed. The tube was then cooled on ice for 30 min.

The potassium-SDS was precipitated and centrifuged for 15 min at 4° C. The supernatant was transferred to a clean 1.5 ml tube, and repeatedly extracted with phenol:chloroform until the color disappeared and the interface was clean. An ethanol precipitation was performed and the solution was centrifuged for 5 min at room temperature to recover DNA.

Transformants were analyzed for the presence of the introduced hygromycin gene. The total DNA was quantitated and cut using the restriction enzyme TAQ 1. The DNA fragments were separated using horizontal gel (0.7% agarose) electrophoresis at 70 V for about 3 hrs and transferred to a Biorad Zeta Probe membrane. The alkaline blotting procedure for DNA capillary transfer was followed, as specified in the Biorad Zeta Probe Blotting Membranes Instruction Manual and set forth below:

1. DNA was depurinated by soaking the gel in 0.25M HCl for 10–15 min.
2. Cut four sheets of Whatman 3MM paper so that they overhang the bottom of the gel tray by 5 cm on each end. Pre-wet the Zeta-Probe membrane in distilled water.
3. Place the four sheets of Whatman 3MM paper on an inverted gel casting tray. Place the 3MM/tray in the bottom of a deep dish. Then saturate the 3MM with 0.4M NaOH. Remove bubbles by repeatedly rolling a test tube over the saturated 3MM. Pour enough NaOH into the deep dish so that the 3MM wick ends are immersed in NaOH.
4. Pour more NaOH onto the 3MM wick to saturate it, then carefully place the gel on the 3MM. Make sure that no bubbles are trapped beneath the gel. Cover the gel with a small amount of NaOH.
5. Place Saran Wrap plastic wrap over the entire gel/3MM stack. Cut out a window with a razor blade, allowing only the gel to emerge.
6. Lower the sheet of pre-wetted Zeta Probe membrane onto the gel surface, making first contact in the center, then allowing the edges to gradually fold down. Carefully flood the filter surface with NaOH. Make sure that no bubbles are present between the gel and the Zeta-Probe membrane.
7. Cut two pieces of 3MM exactly to the gel size. Wet a sheet of pre-cut 3MM paper in water and place it on the Zeta-Probe membrane/gel stack, then repeat with a second sheet.
8. Place a stack of pre-cut paper towels on the 3MM/Zeta-Probe membrane/gel stack. Cover the paper towel stack with a glass plate. Tape the plate to the edges of the transfer dish, putting pressure on the stack. Add a small weight to the plate.
9. Continue transferring for 2–24 hours, depending on the gel concentration and fragment size.
10. After transfer, remove the stack of paper towels. Gently peel the Zeta-Probe membrane from the surface of the gel, rinse it in 2×SSPE and air dry. DNA is fixed to the membrane during transfer.

Hybridization

Prehybridtzation

1. Seal blotted Zeta-Probe membrane inside a heat-sealable plastic bag. Prepare the following solution for pre-hybridization.

1.5 SSPE
   1.0% SDS
   0.5% BLOTTO
   0.5 mg/ml carrier DNA

The carrier DNA must be denatured, before adding it to the hybridization solution, by heating at 100° C. for 5 min., followed by rapid cooling in ice.
2. Cut one corner of the plastic bag and pipet prehybridization solution in, then reseal the bag.
3. Incubate at 65° C. for 0.5–24 hrs.

Hybridization

1. Immediately before use, fragment and denature the probe and carrier DNA. Dissolve the radio-labeled probe in 0.1 ml of 0.2M NaOH, add 0.5 ml carrier DNA (10 mg/ml), mix, and centrifuge briefly to consolidate the solution. Pierce a fine hole in the tube cap. Place the tube in a heating block at 100° C. for 5 min., followed by rapid cooling in ice.
2. Cut one corner of the plastic bag, add probe, then seal the open corner (taking care to exclude all air bubbles). Mix the contents of the bag thoroughly. Incubate at 68° C. for 4-24 hrs. with agitation.

Washes

1. At the completion of hybridization, remove the membranes from their hybridization bags and place them in 2×SSC. Rinse briefly, then wash them successively by vigorous agitation at room temperature for 15 min. in each of the following solutions:
   2×SSC/0.1% SDS
   0.5×SSC/0.1% SDS
   0.1×SSC/0.1% SDS
2. After washing, the blotted membranes are ready for autoradiography.

An isolated 1 kb fragment of the hygromycin gene was labelled with 32-P CTP according to the low melt agarose procedure given in the Amersham Multiprime DNA Labelling Systems Manual (see below). Diagnostic 1.4 and 0.7 kb fragments were present in the DNA of transformed plants and absent from control DNA.

DNA Labelling Protocol

Figure 2:
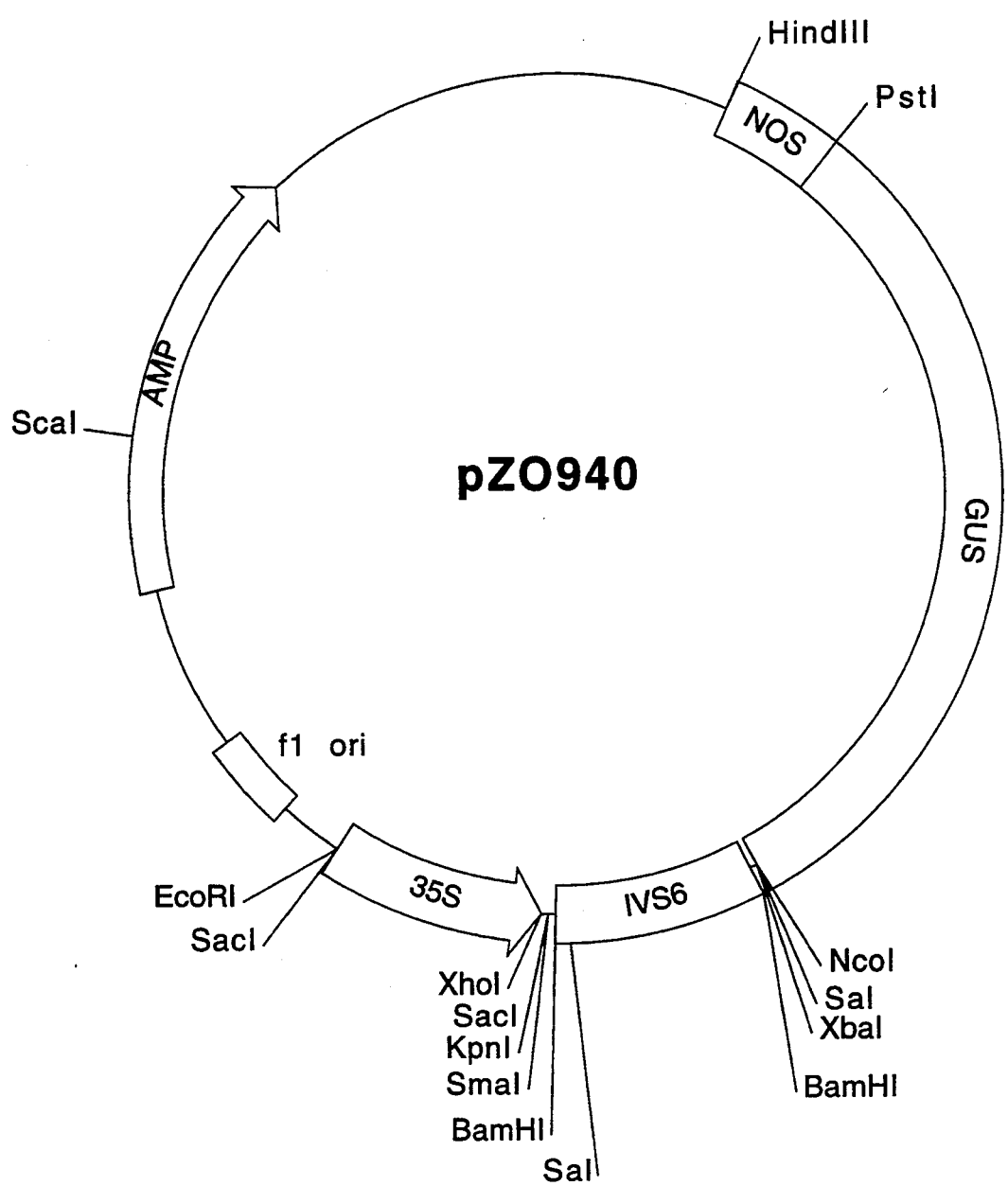
FIG. 2 shows a plasmid map for plant transformation vector p ZO 940.

1. Dissolve the DNA to be labelled to a concentration of 25 μg/ml in either distilled water or 10 mM Tris-HCl, pH 8.0, and 1 mM EDTA.
2. Denature the DNA sample by heating to 95°-100° C. for two min. in a boiling water bath, then chill on ice.
3. Add the appropriate volume of each reagent in the following order (solutions, tables and figures are found in the Amersham DNA Labelling Systems Manual):

|  | RPN.1600 | RPN.1601 |
|---|---|---|
| DNA solution (25 ng)* | 1-10 ul | 1-10 ul |
| Buffer (solution 1) | — | 10 ul |
| Unlabelled dNTPs (solutions 1a-1d) | 4 ul of each, omitting those to be used as label | — |
| Buffer (solution 1e) | 5 ul | — |
| Primer (solution 2) | 5 ul | 5 ul |
| Water | as appropriate for final reaction volume of 50 ul | |
| Radiolabelled dNTP(s) | refer to table 1 and FIGS. 2, 3 and 4 | |
| Enzyme (solution 3) | 2 ul | 2 ul |

*The reaction volume may be scaled up or down if more or less than 25 ng of DNA is to be labelled.

4. Incubate at room temperature overnight.
5. Clean up with elutip to remove unlabelled nDTPs.
6. Denature and add to hybridization solution.
7. Hybridize as described in BioRad protocol (above).

EXAMPLE 5

Following the procedures of Example 1, Stage 3 excised corn embryos and the transforming solution comprising 15 μl (10 ug) of pZ033 plasmid DNA, tracking dye and 2% DMSO are placed in a 0.7% agarose gel in an electrophoresis system apparatus and exposed to an electric current of 52 V for 13 min.

Following exposure, the embryos are rinsed with sterile liquid CM(30) medium and placed on solid CM(30) medium. No attempt was made to select for the exogenous DNA. The resulting seedlings are raised in the normal manner to adult corn plants, which are then cross-pollinated to give F₁ plants. Seeds from the cobs of the F₁ plants are germinated and grown for 1 week and then sacrificed for use in the CAT assays. Additional seeds from the resulting potentially positive cobs are planted and the roots from the resulting plants are harvested and tested in the CAT assay. Of the first eight potentially transformed cobs, two showed transformation.

Leaves of CAT positive F-1 transformants are analyzed for the presence of the introduced CAT gene sequences. Procedures for extracting, cutting, separating, blotting, and probing the DNA were consistant with those given in Ex. 4. A diagnostic 1.2 kb fragment is released whenever the pZ033 (35S-CAT-NOS) plasmid or genomic DNA transformed with the plasmid is cut with the restriction enzymes Hind III and ECO RV and probed with the CAT gene. In this progeny family, the 1.2 kb fragment is always associated with a 1.4 kb fragment. The DNA extracted from the tassel used to produce this F-1 family and from all positive individuals contained the 1.2 kb and 1.4 kb fragments. In contrast, all controls (nuclear DNA from 3780, total DNA from 3780 and F-1 hybrid 3780) lack these fragments.

Plasmid pZ033 comprises a CaMV 35S promoter (nucleotides 7069 to 7569) in the SacI site of pUC19 (commercially available from Bethesda Research Laboratories), the 773 bp chloramphenicol acetyl transferase (CAT) gene from Tn9 [see, Alton and Vapnek, *Nature (London)* 282:864-869 (1979)] whose TaqI ends are changed to PstI, in the Pst site, and a 3' nopaline synthetase polyadenylation sequence (3' nos) (nucleotides 682 to 437) between the PstI and the HindIII sites.

The CAT assay is as follows:

CAT ASSAY

1. Extraction of seedling or other tissue
   A. Seedling or tissue is ground in 150 μl (or multiple thereof) 0.25M Tris-HCl pH 7.8.
   B. Sample is sonicated—3 pulses #2 setting—on ice.
   C. Sample is centrifuged for 3 min. at 12 kg and supernatant transferred to a clean tube.
   D. Sample heated to 65° in water bath for 12 min., then cooled to room temp. (15 on bench).
   E. Sample centrifuged for 30 sec. supernatant pulled and used for CAT assay.

Set up one tube for each reaction. Also set up a control tube for the CAT from E. coli. (13×100 cm tubes).

|  | Negative Control | Potential Plasmid 1 | Positive CAT Control |
|---|---|---|---|
| Supernatant | 100 ul | 100 ul | — |
| 10 mM Tris pH 7.8 | — | — | 99 ul |
| CAT (0.5 unit/ul) | — | — | 1 ul |
| *¹⁴C-Chloramphenicol | 3 ul | 3 ul | 3 ul |
| H₂O | 57 ul | 57 ul | 57 ul |

Incubate 5 min. at 37° C. (this is to bring rxn. mix to incubation temperature). Then add:

| 4 mM Acetyl CoA | 20 ul | 20 ul | 20 ul |
|---|---|---|---|
|  | 180 ul | 180 ul | 180 ul |

3. Incubate samples at 37° C. for 1-2 hours.
4. Stop reaction with 2 ml cold water-saturated ethyl acetate. Add 1 ml H₂O to make the interface more visible.

5. Cover tube with parafilm and vortex on #1 for approximately one minute.
6. Spin in IEC for 3–5 min. on #5.
7. Transfer top layer to small tubes (13×75).
8. Dry under $N_2$ in hood till dry (approximately 45 minutes; avoid overdrying).
9. While samples are drying, prepare the TLC tank with solvent: 100 ml of 95:5 chloroform:methanol. Place a wick in the tank for all sides.
10. Prepare a 20×20 cm silica 60 gel TLC plate. Mark a line in pencil 1.5 cm from the bottom. Mark sample positions with intersecting lines. Separation is by ascending chromatography.
11. After the samples have dried down, resuspend them in 30 $\mu$l of ethyl acetate (not water saturated).
12. Spot samples in very small area with a 10 $\mu$l micropipet. Have a hair dryer blowing over the plate while spotting.
13. Place plate in the tank and let solvent front reach approx. 3 mm from the top of the plate (40–50 minutes).
14. Let the plate air dry for fifteen or twenty minutes in the hood, then place in a cassette with a piece of film (preflashed) at room temperature overnight.
15. Develop the film the next day. Put down again for a longer exposure if needed.

EXAMPLE 6

Following the procedures of Example 1, tomato embryos (Burpee's Super Beefsteak VFN) are placed in the wells of a 0.7% agarose gel in a horizontal electrophoresis system beside the wells containing a transformation solution comprising 10 ug of pZO 60 or pZO 67 plasmid DNA, 2% DMSO and bromophenol blue tracking dye. The embryos are exposed to a continuous electric current of 52 V for about 15 min.

After electrotransformation, the embryos are removed to tomato media for 2–3 days recovery. Then, they are placed on selective tomato media which contains 25 ug/ml hygromycin for 10 days. None of the untreated control seedlings survived this selection. Transformants are rescued to tomato media containing 0.5 mg/l indoleacetic acid (IAA) and rooted before being transplanted into soil.

Leaves of these primary transformants are analyzed for the presence of introduced DNA, specifically the hygromycin gene. Total DNA is isolated from the plant tissue, cut with the restriction enzyme TAQ I, separated, blotted and hybridized as detailed in Example 4. Diagnostic hygromycin fragments (1.4, 0.7 and 0.4 kb) were present in the DNA of transformed plants and absent from the control DNA.

The plasmid pZO 60 comprises the plasmid pUC 8 with the 35S promoter, HPT coding sequence, and the nos terminator of pZO 25 (see Example 4) immediately followed (in tandem) by a second copy of the 35S promoter, the CAT coding sequence of pZO 33 (see Example 5) and a second copy of the nos terminator.

The plasmid pZO 67 consists of the plasmid pUG 8 with the 35S promoter of HS83E (see Example 1), the B-glucuronidase (GUS) coding region on a Pst I fragment from pRAJ-260 [Jefferson, R. A., Burgess, S. M. and Hirsch, D., Proc. Natl. Acad. Sci. USA 83:8447–8451 (1986)], and the nos terminator, immediately followed (in tandem) by the 35S promoter, HPT sequence, and nos terminator of pZO 25 (see Example 4).

EXAMPLE 7

Following the procedures of Example 1, stage 3 corn embryos are placed in the wells of a 0.7% agarose gel in a horizontal electrophoresis system beside the wells containing a transformation solution comprising 10 ug of B.t.k./HPT plasmid (pZO 85-BTK/HPT) DNA, 2% DMSO and bromophenol blue tracking dye. The embryos are exposed to a continuous electric current of 52 V for about 15 min., after which they are removed to CM(30) medium and selected for acquired hygromycin resistance. Those seedlings showing resistance are raised to larger seedlings and tested by standard bioassay procedures for resistance to the tobacco budworm (*Heliothis virescens*). *Bacillus thuringiensis* var. kurstaki (B.t.k.) produces an insecticidal toxin active against the tobacco budworm which is a pest not only in tobacco but in corn and cotton as well.

The plasmid pZO 85 is constructed as follows. The SalI-EcoRI fragment containing the $\beta$-glucuronidase (GUS) coding sequence from pRAJ 275 (commercially available from Clontech Laboratories) was modified to change the EcoRI site at the 3' end to a PstI site. A feature of this GUS gene is that an NcoI site straddles the initiator codon (ATG) of the coding sequence. pZO 85 consists of the 35S promoter and nos sequences as found in pZO 33 (see Example 5) and the Sal-Pst fragment described above (in place of the CAT gene).

pZO 85-BTK/HPT is prepared by substituting the Nco-Pst fragment of pAMVBTS containing a modified B.t.k. sequence [Barton et al., *Plant Physiol.* 85:1103 (1987)] for the NcoI-PstI fragment of pZO 85. This sequence is immediately followed (in tandem) by the 35S promoter and nos terminator of pZO 33 (see Example 5) with the HPT sequence of pZO 25 (see Example 4).

EXAMPLE 8

Following the procedures of Example 1, Stage 3 corn embryos are placed in the wells of a 0.7% agarose gel in a horizontal electrophoresis system beside the wells containing a transformation solution comprising 10 ug of B.t.t./HPT plasmid (PZO 85-BTT/HPT) DNA, 2% DMSO and bromophenol blue tracking dye. The embryos are exposed to a continuous electric current of 52 V for about 15 min., after which they are removed to CM(30) medium and selected for acquired hygromycin resistance. Those seedlings showing resistance are raised to larger seedlings and tested by standard bioassay procedures for resistance to the corn root worm (Diabrotica spp.). *Bacillus thuringiensis* var. tenebrionis (B.t.t.) produces an insecticidal toxin active against coleopteran insects, of which corn root worm is an example.

pZO 85-BTT/HPT is prepared by substituting the Nco-Pst fragment of a modified B.t.t. sequence [see Sekar et al., *Proc. Natl. Acad. Sci.* 84:7036–7040 (1987)], which has been modified at the ATG start codon to contain a NcoI site and at the 3' terminus of the coding region to produce a PstI site, for the Nco-Pst fragment of pZO 85 (see Example 7). This sequence is immediately followed (in tandem) by the 35S promoter and nos terminator of pZO 33 (see Example 5) with the HPT sequence of pZO 25 (see Example 4).

EXAMPLE 9

In order to optimize each of the factors which could influence the frequency of transformation it is necessary to have an assay which allows for a rapid and reliable indicator of successful transformation.

This is achieved by employing plasmid DNA containing β-glucuronidase (GUS)-gene which readily lends itself to various assaying techniques (cf R. A. Jefferson, Plant Molecular Biology Reporter 5(4), pp 387–405, 1987) including the histochemical assay described below. The DNA employed (pZ0106 and pZ0940) is shown in FIGS. 1 and 2.

PROCEDURES

Standard materials and conditions for ET are used in 16 initial experiments. Standard materials are stage 3 sweet corn embryos and standard conditions include digestion of the embryos with BMS protoplasting medium (PE Table D) for 20 minutes and directional electrophoresis in 1X TAE at 4 V/cm for 20 minutes. The transformation solution which contained 2% DMSO and 10 μg plasmid DNA (pZO 1016, 35S-IVS6-GUS-NOS) per embryo is loaded into an agarose well and electrophoresced into (and past) a second agarose well containing the digested embryo. Following transformation, the embryos are cultured on modified MS medium (CM(30) Table A) (Green and Phillips, Crop Science 15 pp 417–421 1975) in a growth room. Embryos are either assayed for GUS activity after 48 hours or scored for viability, normal shoot and root development, and chlorophyll production after at least five days in culture. Although GUS activity is fully visible within 24 hours, after 48 hours both shoots and roots have elongated away from the scutellum which allows more accurate mapping of ET events.

In experiments designed to optimize ET, one experimental condition is altered at a time; all other conditions remained the same unless noted. The first experiment investigates the length of time that the embryos are digested before ET. The embryos are agitated in PE for 20, 35, 50, 65 or 90 minutes and electrotransformed using the standard conditions above. In the second set of experiments, plasmid DNA concentrations of 2.5, 5 or 10 μg per embryo are tested using the optimized digestion regime. Orientation of the embryos is examined by facing either the embryo or the keel of the scutellum towards the transformation solution during electrophorests.

The fourth parameter is amount and duration of voltage. Initially, embryos are subjected to a range of voltages, from 4 V/cm to 7 V/cm, to identify voltages which would preserve reasonable viability (at least 90% survival). Then using the optimum digestion time and amount of DNA, embryos are treated for 20, 35, 50 or 65 minutes at either 4 V/cm or 5 V/cm. The next condition examines ET frequency following digestion of the embryos with cellulase from Calbiochem, Worthington or Yakult substituted by weight into PE. The form of the DNA used in ET experiments is tested by comparing the frequency of ET events in embryos treated with equimolar concentrations of double-stranded DNA (pZO 1016) or single-stranded, antisense DNA (pZO 940) both circular and coding for β-glucuronidase. After combining all the best conditions from the previous experiments, the necessity of including 2% DMSO in the transformation solution is reexamined. ET is optimized using the best conditions above.

Embryos displaying ET events are accumulated in ethanol, and the position of the cells displaying GUS activity is mapped on a diagram of the stage 3 embryo. The frequency of ET events in the embryo (shoot, transition zone, or root) and scutellum (subembryo, exposed surface, or keel) is calculated. Finally, experiments are designed to optimize the number of shoot transformation events. This is accomplished by removing a large proportion of the coleoptyle and scutellum before the embryos are digested and by orienting these embryos sideways in the gel lane with the cut edge/shoot apex pointed toward the advancing current and transformation solution.

Gus-Assay

1. Place fresh tissue (whole embryos) in microliter wells and cover with staining solution (50 to 100 μL per well) taking care that tissue remains submerged during infiltration.
2. Incubate tissues at 37° C. for 2 to 4 hours. Cover (with parafilm or plate lid) to avoid evaporation. Strong expression will be visible within this period. Weaker expression may need overnight incubation to be clearly seen.
3. Examine on dissecting scope. If pigments interfere, fix for 24 hours in FAA (85 ml of 50% ethanol, 5 ml of glacial acetic acid, 10 ml of formalin) or Farmer's fixative (25 ml of glacial acetic acid, 75 ml of ethanol) to remove chlorophyll and carotinolds.

| X-Gluc Staining Solution | |
| --- | --- |
| Stocks | Volume (ml) |
| 0.2 M NaPO4 buffer, pH 7.0 (0.2 M Na2HPO4: 62 ml 0.2 M NaH2PO4: 38 ml) | 2.5 ml |
| dH2O | 2.3 ml |
| 0.1 M K3pFe(CN)6] | 0.25 ml |
| 0.1 M K4 [Fe(CN)6].3 H2O | 0.25 ml |
| 1.0 M Na2EDTA | 0.50 ml |
| 10% Triton X100 | 0.10 ml |

Dissolve 5 mg of X-gluc in 20 μl of formamide. Add to solution. (X-gluc - 5-bromo-4-chloro-3-indolyl glucuronide.)

Results

The first experiments alter the length of time that stage 3 embryos are digested. As based on visible, transient gene expression events, the embryos which are digested for 50 minutes give 65% higher mean frequencies and 90% viability.

Using transformation solutions containing 2.5, 5.0 and 10 μg DNA per embryo, three early experiments and two later ones differing by digestion times of 20 minutes and 50 minutes, respectively, show no difference in ET frequency between treatments. The only significant difference (p=0.01) between experiments is due to digestion time. Digestion for 50 minutes produces a 57% greater mean frequency. Successive experiments used 50 minutes digestion and less DNA, 5 μg per embryo/cell.

Embryo orientation is investigated by placing either the embryonic axis or the keel of the scutellum towards the transformation solution. Under standard conditions, only the embryo and front side of the scutellum appear to be fully receptive to transformation.

Because viability is reduced at the higher end of the voltage range, ET experiments are limited to 4 V/cm and 5 V/cm for 20, 35, 50 or 65 minutes. ET at 4 V/cm for 20 minutes gives the highest transformation rate.

In four experiments of 50 embryos per treatment, three sources of cellulase are substituted by weight into PE or used alone to digest the embryos prior to ET.

Digestion with Calbiochem cellulase in the PE give the highest ET frequency. Experiments using double-stranded and single-stranded, antisense DNA give mean ET frequencies of 28.9% and 2.9% respectively.

In experiments using 100 predigested, healthy embryos (50 with and 50 without DMSO), the frequency of ET using 2% DMSO was not significantly different from experiments done in the absence of DMSO.

ET events were 2.5 times more common in the tissues of the developing embryo than in the scutellum and most common, 53.8% in coleoptyle/shoot tissues.

From these mapping studies, it is clear that only slightly more than half of the transient ET events affected the shoot axis. The final set of experiments is designed to optimize shoot transformation by the simple removal of other receptive tissues and maximizing exposure of the shoot apex. Specifically, a large proportion of the coleoptyle and scutellum is cut away from each embryo prior to digestion, and that cut surface is oriented in the gel well toward the advancing transformation solution. Among 153 embryos, 15 out of 17 ET events affected shoot tissues.

The following is a non-limiting recital of some of the specific embodiments of the invention.

We claim:

1. A method for transforming non-protoplastic plant tissue and cells comprising contacting the tissue and cells with a transformation solution comprising DNA within a horizontal electrophoresis gel in the presence of a non-pulsed electric current which is less than about 200 volts for a time sufficient to effect uptake and integration of the DNA into the plant tissue or cells.

2. The method of claim 1 wherein the DNA is vector DNA.

3. The method of claim 2 wherein the vector DNA is a plasmid.

4. A method according to claim 3 wherein the plasmid further comprises a *Bacillus thuringiensis* insecticidal toxin gene.

5. A method according to claim 3 wherein the plasmid further comprises a gene which confers herbicide resistance.

6. The method of claim 1 in which the plant tissues or cells to be transformed and the DNA are placed in separate parallel in wells such that the electric current will run in a direction from the DNA to the plant cells.

7. The method of claim 1 wherein the transformation solution contains a membrane-permeating agent.

8. The method of claim 7 wherein the membrane-permeating agent is a polar membrane-permeating agent.

9. A method according to claim 8 wherein the polar membrane-permeating agent is selected from the group consisting of dimethyl sulfoxide, lysolecithin, sodium dodecyl sulphate and Triton X.

10. The method of claim 1 wherein the plant tissue or cells is selected from the group consisting of embryos, meristematic tissue, axillary buds, stem strips, cell suspensions and callus.

11. The method of claim 10 wherein the plant tissue or cells is from a corn plant.

12. A method according to claim 10 wherein the plant tissue or cells is from a tomato plant.

13. A method according to claim 1 wherein the voltage of the electrical current is from 50 V to 110 V.

14. A method according to claim 1 wherein the current is present from about 5 to about 25 minutes.

15. A method of producing transformed fertile plants which comprises
 a) placing non-protoplastic plant tissue or cells to be transformed into a first well of a horizontal electrophoresis gel;
 b) placing a transformation solution comprising DNA; into a second well that is parallel to the first well
 c) exposing said gel comprising the plant tissue or cells and transformation solution to a non-pulsed electric current which is less than about 200 volts for a period of time sufficient to move the DNA to the plant tissue or cells and effect uptake and integration of the DNA into said plant tissue or cells;
 d) obtaining transformed plant tissue or cells; and
 e) regenerating from the transformed plant tissue or cells genetically transformed fertile plants.

16. A method according to claim 15 wherein the transformed fertile plant is a monocotyledonous plant.

17. A method according to claim 16 wherein the plant is corn.

18. A method according to claim 15 wherein the transformed fertile plant is a dicotyledonous plant.

* * * * *